United States Patent [19]

Rogers

[11] Patent Number: 4,510,937
[45] Date of Patent: Apr. 16, 1985

[54] METHOD AND APPARATUS FOR OPERATING DUAL DIATHERMY APPLICATOR HEADS IN CLOSE PROXIMITY TO ONE ANOTHER

[75] Inventor: Noel A. Rogers, Shawnee Mission, Kans.

[73] Assignee: International Medical Electronics, Ltd., Kansas City, Mo.

[21] Appl. No.: 546,559

[22] Filed: Oct. 28, 1983

[51] Int. Cl.³ .............................................. A61N 1/40
[52] U.S. Cl. ..................................................... 128/422
[58] Field of Search ................................ 128/422, 804

[56] References Cited

U.S. PATENT DOCUMENTS

| 3,058,470 | 10/1962 | Seeliger et al. | 128/422 |
| 3,675,655 | 7/1972 | Sittner | 128/422 |
| 3,800,802 | 4/1974 | Berry et al. | 128/422 |
| 4,095,602 | 6/1978 | Leveen | 128/804 |
| 4,210,152 | 7/1980 | Berry | 128/422 |
| 4,285,346 | 8/1981 | Armitage | 128/422 |

FOREIGN PATENT DOCUMENTS 610878 3/1935 Fed. Rep. of Germany ...... 128/422
2307520 11/1976 France ........................... 128/419 PS Primary Examiner—William E. Kamm
Attorney, Agent, or Firm—Kokjer, Kircher, Bradley, Wharton, Bowman & Johnson

[57] ABSTRACT

A method and apparatus for simultaneously operating two diathermy treatment heads in close proximity without interference caused by phase and frequency differences. Each diathermy head has a drive circuit powered by a master oscillator providing RF energy. Each head can be used alone with RF drive from its own oscillator. When the heads are to be used in close proximity, they are coupled by coaxial cable, and one oscillator is automatically disabled to permit the other oscillator to furnish the RF drive for both systems. The RF drive is then coherent in phase and frequency in both systems, so the two diathermy heads do not "fight" each other.

9 Claims, 4 Drawing Figures

METHOD AND APPARATUS FOR OPERATING DUAL DIATHERMY APPLICATOR HEADS IN CLOSE PROXIMITY TO ONE ANOTHER

BACKGROUND OF THE INVENTION

This invention relates generally to diathermy equipment and more particularly to an arrangement which permits two diathermy applicator heads to be used in close proximity without adversely effecting one another.

U.S. Pat. Nos. 3,800,802 and 4,210,152 to Berry disclose diathermy machines which are used to apply RF energy to the human body for therapeutic purposes. As described in these patents, a diathermy treatment head which applies RF energy to the patient produces both electromagnetic and electrostatic energy. Only the electromagnetic energy is useful in therapy. The electrostatic field simply heats the surface area of the skin without deep penetration and is therefore undesirable. Electrostatic shields of the type shown in the additional Berry patent Nos. 4,068,292 and 4,281,362 are normally used to attenuate the electrostatic field.

In order to properly and efficiently utilize the electromagnetic field that is generated by the applicator head, the circuitry should be tuned and the power applied to the patient should be closely controlled at the desired level. As the patient moves or the body temperature or circulation changes, the load can vary rather widely. To compensate for such expected changes in the load, automatic tuning devices are desirable because they continuously maintain the head tuned to a resonant condition to assure maximum power transfer from the applicator head to the patient load.

Although continuously tuned applicator heads have performed in a satisfactory manner for the most part, problems have been encountered when two applicator heads are used in close proximity to one another. This most often occurs when two different areas of the body are to be treated simultaneously by two different applicator head which may or may not be part of the same diathermy machine. The operation of two treatment heads in close proximity results in the two heads "cross talking" or "fighting" with each other. This type of interference is most prevalent when the two heads apply different amounts of power at different pulse rates, although it is also a factor when the heads operate at the same power level and rate. Physically, what happens is that the magnetic field generated by each applicator head interferes with the other head and particularly its power sense and tuning circuits. The interference causes the tuning systems to attempt to retune the applicator heads and continuously "hunt" for a resonant condition. Due to the differences in the phase and frequency of the excitation current, the tuning systems have a tendency to oscillate which causes inefficiencies and other undesirable operating characteristics of the diathermy equipment. The end result is that the output power from each applicator head is different from what it should be for effective therapy. At the same time, energy is inefficiently transferred from the applicator head to the patient due to the untuned state of both applicator heads and the continuous oscillation of the tuning circuits.

SUMMARY OF THE INVENTION

The present invention is directed to a diathermy applicator head having improved drive circuitry which permits the applicator head to be used simultaneously with and in close proximity to an identical applicator head without undesirable interaction between the two heads. It is the primary object of the invention to provide an applicator head which can be used either alone or in close proximity to another applicator head. It is another important feature of the invention that the two applicator heads can be operated at the same or at different power levels and pulse rates without adversely affecting one another.

In accordance with the invention, each applicator head has a master oscillator in its drive circuit which is normally enabled to provide the RF drive energy for the applicator head. The master oscillator drives a buffer amplifier which in turn drives a multiple stage RF power amplifier. The power amplifier drives the applicator head through a power sense circuit which senses the amount of power delivered to the head and provides this information in digital form to a central processor. The processor applies a keying pulse which determines the amount of power delivered by the power amplifier, and if a power adjustment is indicated, the processor makes the adjustment to achieve a power level which conforms with the desired power level that has been keyed into the power set register of the processor.

In order to prevent interference between two applicator heads that are used in close proximity, each drive circuit is provided with two terminals which can be connected with the terminals of the other applicator head. When so connected, the master oscillator of one circuit is disabled and the other oscillator drives both circuits. The second set of connected terminals provides a circuit path for application of the buffered output signal from one buffer amplifier to both power amplifiers so that both applicator heads are driven by the same RF energy at the same phase and frequency. The phase and frequency coherence prevents the two applicator heads from "fighting" and allows the tuning circuits to retune for normal load changes caused by patient movement or temperature and/or circulation changes.

Consequently, the automatic tuning systems of the applicator heads can react without "fighting" one another, and the applicator heads can be continuously tuned to a resonant condition for maximum power transfer. At the same time, the applicator heads can be operated at different power levels and at different pulse rates without disruption of the tuning systems.

DETAILED DESCRIPTION OF THE INVENTION

Figure 1:
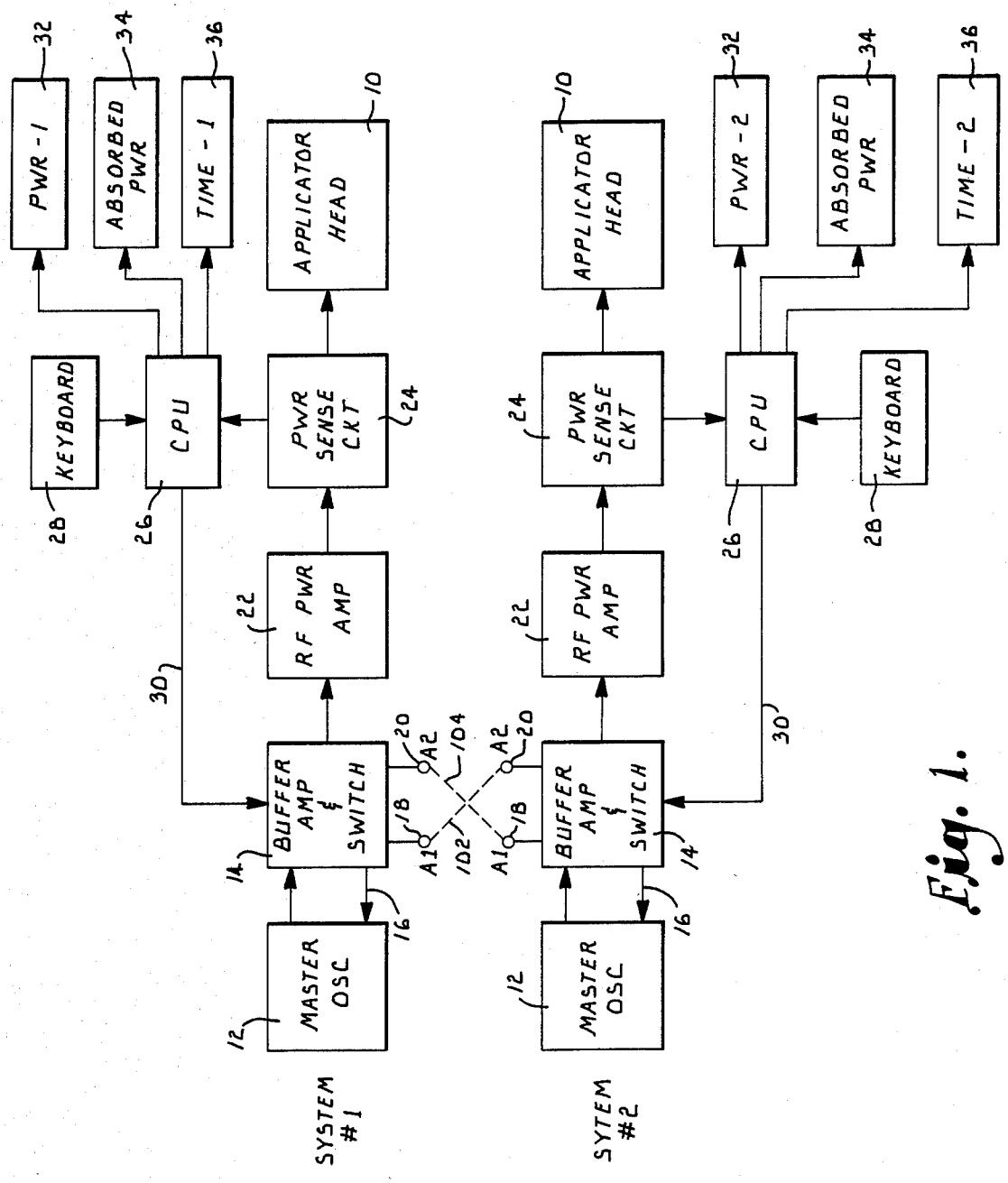
Figure 2A:
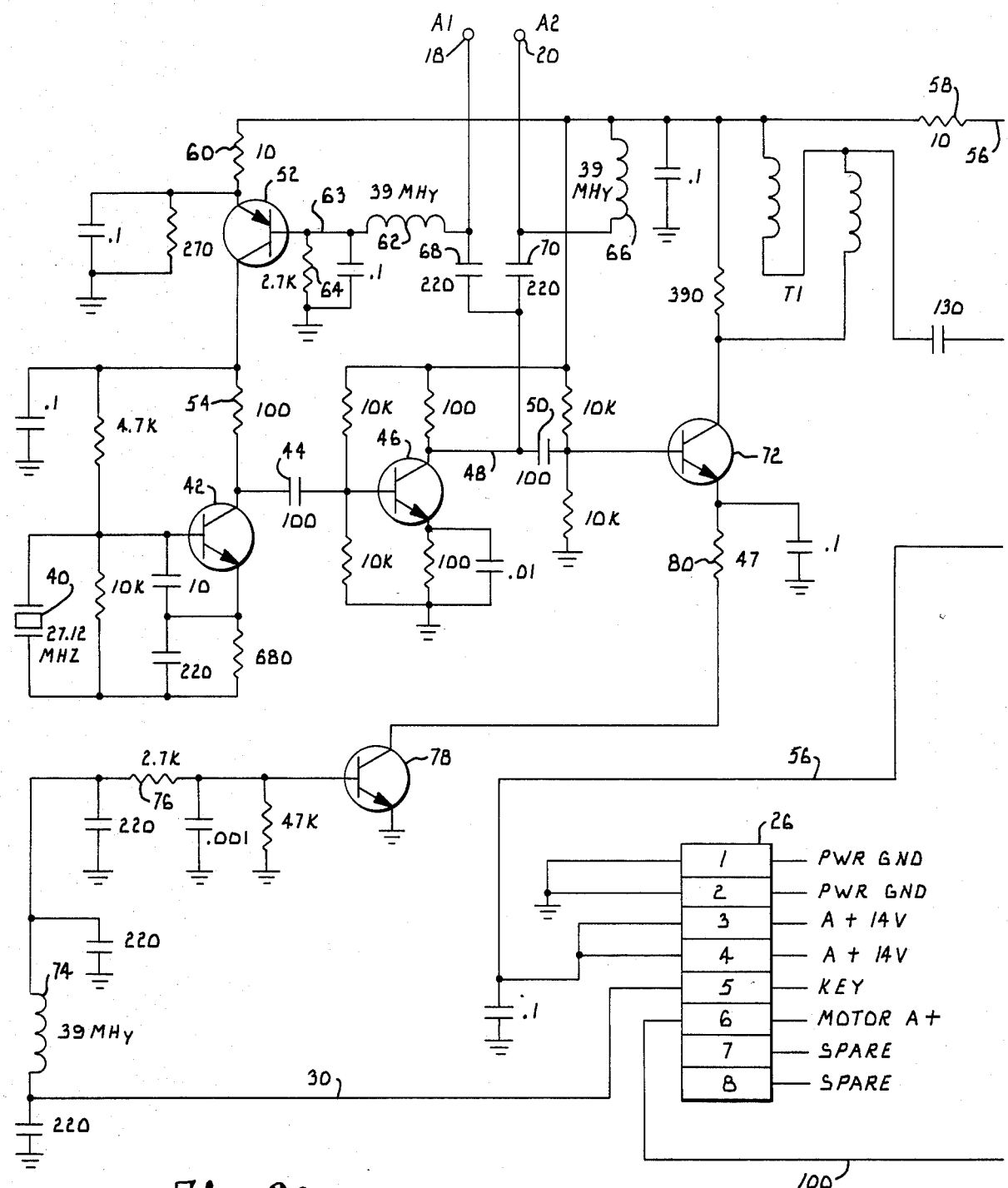
Figure 2B:
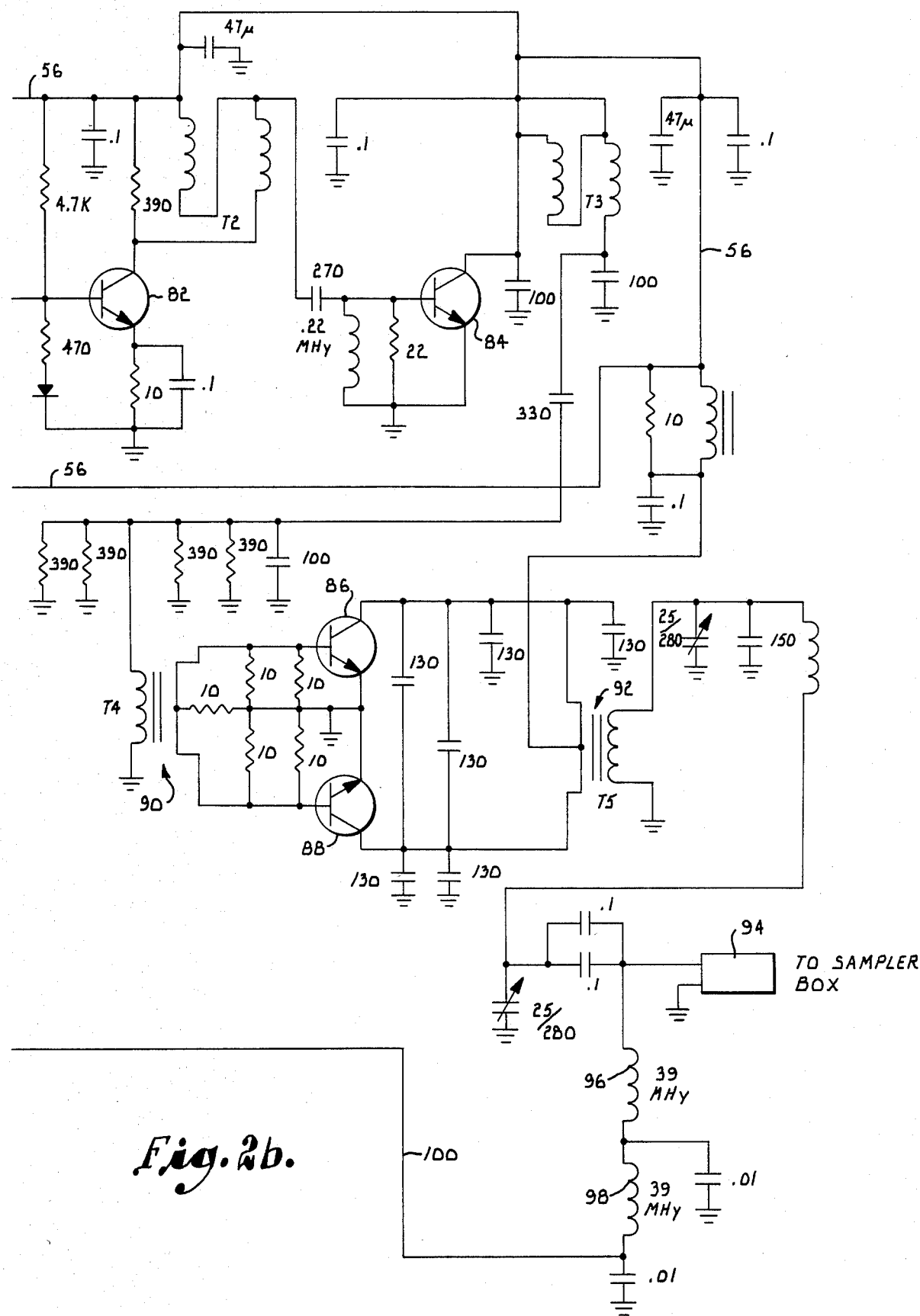

In the accompany drawings which form a part of the specification and are to be read in conjunction therewith and in which like reference numerals are used to indicate like parts in the various views:

FIG. 1 is a block diagram showing two diathermy applicator heads and the related drive circuits included in a diathermy apparatus constructed in accordance with a preferred embodiment of the present invention;

FIGS. 2a and 2b together form a schematic diagram of the drive circuitry for one of the applicator heads; and FIG. 2c is an organizational diagram showing the manner in which FIGS. 2a and 2b are to be arranged.

Referring now to the drawings in detail and initially to the block diagram of FIG. 1, the diathermy apparatus of the present invention is similar to the apparatus shown in U.S. Pat. Nos. 4,210,152 to Fred M. Berry and 3,800,802 to Berry et al., both of which are incorporated herein by reference. The present invention provides an improvement in diathermy apparatus of this type and is directed more particularly to circuitry which permits two applicator heads 10 to be used in close proximity without interference or other adverse effects in the tuning systems.

As explained in the aforementioned patents, each diathermy applicator head 10 has an inductive coil which generates electrostatic and electomagnetic fields when high frequency currents are applied to the coil by its drive circuit. It has become common for the electrostatic field to be attenuated by an electrostatic shield such as a shield of the type shown in U.S. Pat. No. 4,281,362 to Berry or U.S. Pat. No. 4,068,292 to Berry et al. These shields significantly reduce the undesirable effects of the electrostatic field, including surface heating of the skin of the patient and capacitive coupling between the patient's body and the diathermy treatment head.

It has also become common for the applicator head to be equipped with an automatic tuning system which maintains the applicator head in electrical resonance by keeping the current and voltage in phase so that optimum energy transfer is achieved between the applicator head 10 and the patient. It is contemplated that the diathermy apparatus of the present invention will be provided with an automatic tuning system and that an electrostatic shield incorporated into the applicator head 10.

In accordance with the present invention, two diathermy applicator heads 10 (identified in FIG. 1 as "System #1" and "System #2") are identical to one another, and each is controlled by drive circuitry which includes a master oscillator 12. Each master oscillator 12 drives a buffer amplifier and switching circuit 14, the switching portion of which controls the operation of the oscillator as indicated by line 16. Each circuit 14 has an A1 terminal 18 and an A2 terminal 20 which are used to connect the two diathermy systems together when the two applicator heads are to be used in close proximity.

Each circuit 14 drives an RF power amplifier 22 which includes a number of amplifier stages, as will be explained in more detail. The output from each amplifier 22 is applied to the applicator head 10 through a power sense circuit 24 which senses the amount of power that is being applied to the applicator head and converts this information to digital form. The digital data is delivered to a central processing unit 26 which preferably takes the form of a microprocessor programmed to perform the desired functions. The CPU 26 compares the power actually applid to the applicator head with a desired power level which is entered by a keyboard 28 into a power set register of the microprocessor. A keying pulse applied by the CPU on a key line 30 is adjusted in its width until the average power delivered to the applicator head by the RF power amplifier 22 conforms with the desired power level setting.

The CPU 24 for each system preferably provides a visual display which includes a power display 32 showing the power setting that has been entered into the microprocessor, an absorbed power display 34 showing the power absorbed by the tissue of the patient, and a time display 36 showing the time period (pulse width) durng which RF power amplifier 22 is keyed on to supply RF energy to the applicator head. The CPU calculates the amount of power absorbed by the patient load by multiplying the measured level of power applied to the applicator head by a fraction obtained by dividing the pulse width (E.G. 1 microsecond) by the pulse rate period (e.g. 2 microseconds).

Referring now to the schematic diagram and particularly to FIG. 2a, the master oscillator for each applicator head includes a quartz crystal 40 and a transistor 42 having its base connected with one side of the crystal. The crystal oscillator produces a signal having a standard frequency of 27.12 megahertz. The output from the crystal oscillator is applied through a 100 picofarad coupling capacitor 44 to the base of a transistor 46 serving as a buffer amplifier. The output from transistor 46 is a buffered output signal applied to a buffer output line 48 containing a 100 picofarad coupling capacitor 50.

The buffer amplifier of circuit 14 is provided by transistor 46 and the associated circuitry, and the switching function is provided by a PNP switching transistor 52. The collector of transistor 52 connects with the collector of transistor 42 through a resistor 54. The CPU 26 supplies dc power on a +14 volt line 56 which connects with the emitter of transistor 52 through a pair of resistors 58 and 60. The base of transistor 52 is connected with the A1 terminal 18 through a choke coil 62 which blocks the RF power. Coil 62 is included in a line 63 which serves as a control line for applying a disable signal to the base of transistor 52. When the A1 terminal 18 is disconnected, the base of transistor 52 is pulled low through resistor 64, and the PNP transistor 52 is then conductive to supply transistor 42 with power from the +14 volt line 56, thereby enabling the master oscillator. When a disable signal is applied to line 63 and through choke 62 to the base of transistor 52, transistor 52 is placed in a nonconductive state to disable the master oscillator.

The A2 terminal 20 is connected with the dc power line 56 through resistor 58 and a choke coil 66 which isolates the dc line from the RF circuitry. Terminals 18 and 20 are coupled with the buffer output line 48 through respective 220 picofarad capacitors 68 and 70.

As previously indicated, the RF power amplifier has multiple stages. The first amplifier stage includes a transistor 72 having its base connected with the buffer output line 48 through the coupling capacitor 50. The key line 30 of the CPU is tied through an inductor 74 and a resistor 76 with the base of a switching transistor 78. When the key line 30 is activated, transistor 78 is conductive and connects the collector of transistor 72 with ground through resistor 80.

The second RF amplifier stage includes a transistor 82 (FIG. 2b) which is coupled through an RCL network with the output line of transistor 72. The output signal from transistor 82 is coupled through another RCL network with another transistor 84. The fourth and final amplifier stage includes transistors 86 and 88 which are coupled with the output line of transistor 84 through an RCL network and a transformer 90.

The output signal from the fourth amplifier stage is coupled through a transformer 92 with a sampler circuit 94 and also with induction coils 96 and 98 which apply the RF energy to the diathermy treatment head. As described in the previously referenced U.S. Pat. No. 4,210,152, the sampler circuit 94 measures the amount of power that is being absorbed by the patient load and also provides a phase control signal which controls a servomotor in a manner to adjust a tuning element in the applicator head so that the head is continuously tuned to a resonant condition. This automatic tuning of the diathermy head results in maximum efficiency and optimum energy transfer from the applicator head to the body tissue that is undergoing treatment.

The power applied to the applicator head is sensed by the power sense circuit and applied to the CPU 26 on line 100. The CPU 26 compares the power signal on line 100 with the desired power level that has been previously entered via the keyboard 28 and, if there is a discrepancy, the pulse applied to the key line 30 is adjusted in its width until the actual power delivered to the applicator head corresponds to the desired power level.

In use, either diathermy system (System #1 or System #2) can be operated alone or simultaneously with and in close proximity to the other applicator head to treat patients. When the unit is operated alone, the A1 and A2 terminals 18 and 20 remain disconnected. Then, the base of transistor 52 is pulled low through resistor 64, and transistor 52 is conductive to enable the oscillator formed by crystal 40, transistor 42 and the associated circuit components.

The RF energy generated by the oscillator is coupled through capacitor 44 to the buffer stage transistor 46. The A1 and A2 terminals 18 and 20 are open, so the output from the buffer transistor 46 is applied from line 48 through capacitor 50 to the initial power amplifier stage transistor 72. Under the control of the keying pulse applied to the key line 30, transistor 78 controls the power amplifier 72. The output from the initial power amplifier stage drives the subsequent stages formed by transistors 82, 84, 86 and 88. The amplifier output signal from these amplifier stages is then delivered to the applicator head which is used to treat the body tissue of the patient.

The power measurement is applied on line 100 to the CPU 26 which compares it to the value that has been entered into the power set register as the desired power level. If the actual power level is less than the programmed power setting, the CPU increases the duration of the keying pulse applied to the key line 30 in order to increase the amount of power delivered to the applicator head. Conversely, if the actual power is greater than the desired power, the duration of the keying pulse is reduced until correspondence is achieved between the actual and desired power levels.

By way of example, at a fixed pulse rate of 500 Hz representing a period of 2 milliseconds, the average power delivered by the power amplifier to the applicator head is 200 watts with an infinite pulse width. If the desired power level is 100 watts, the pulse width should be 50% of 2 milliseconds or 1 millisecond. If the desired power level is 10 watts, the pulse width should be 5% or 100 microseconds. The CPU makes the necessary calculations and keys the key line 30 such that the proper pulse width is achieved for the desired power level.

In this manner, either or both applicator heads can be used separately in the diathermy treatment of patients. Each diathermy system has its own oscillator which serves to generate the RF energy when the applicator head is used alone or at a considerable distance from the other applicator head.

It is often desirable to use the two applicator heads 10 simultaneously to treat nearby areas of a patient. In the past, applicator heads used in close proximity to one another have interacted in a manner to confuse the tuning mechanisms. As a result, there has been a tendency for the applicator heads to continuously hunt for but never achieve optimum tuning, and the efficiency has suffered accordingly.

However, in accordance with the present invention the two applicator heads 10 can be used simultaneously in close proximity without adversely affecting their operation. When the diathermy equipment is to be used as a two head system, the terminals of Systems 1 and 2 are selectively connected by coaxial cables. As shown in FIG. 1, the A1 terminal 18 of System #1 can be connected with the A2 terminal 20 of System #2 by a coaxial cable 102. Alternatively, a coaxial cable 104 can be used to connect the A1 terminal 18 of System #2 with the A2 terminal 20 of System #1.

Referring now to FIGS. 2a and 2b and assuming first that the cable 102 is used to connect the A1 terminal of System #1 with the A2 terminal of System #2, the dc on the +14 volt line 56 of System #2 is applied through resistor 58 and choke 66 to the A2 terminal of System #2, through the coaxial cable 102 to the A1 terminal of System #1, and through choke 62 and the control line 63 to the base of transistor 52 of System #1. Transistor 52 is thus placed in a nonconductive state by the disable signal, and power is removed from the collector of transistor 42. This disables the master oscillator 12 of System #1.

At the same time, transistor 52 of System #2 remains conductive because the A1 terminal 18 remains open and the base of transistor 52 is pulled low. The master oscillator 12 of System #2 is thereby enabled to furnish RF drive energy from its crystal 40 and transistor 42 to its buffer stage transistor 46. The RF energy is further amplified by the amplifier stages and coupled to the applicator head of System #2 in the manner described previously.

The RF energy on the buffer output line 48 of System #2 is also coupled through capacitor 70 to the A2 terminal 20 of System #2, through the coaxial cable 102 to the A1 terminal 18 of System #1, through capacitor 68 to line 48 and through capacitor 50 to the base of transistor 72 of System #1. The RF energy is amplified by the conventional amplifier stages of System #1 and then coupled to its applicator head for treatment of the patient.

In this manner, the master oscillator 12 of System #1 is disabled and the oscillator of System #2 provides the primary drive energy for both applicator heads. Since both applicator heads are driven by the same oscillator, the phase and frequency are coherent in the two systems and there is no adverse interaction or fighting between the two applicator heads. By disabling one oscillator and routing the RF energy of the other oscillator to both power amplifiers simultaneously, the energy applied to and radiated from each applicator head is made to conform in phase and frequency with the RF energy applied to and radiated from the other applicator head. As a result of this correlation in phase and frequency, the two applicator heads do not "fight" or otherwise interfere with one another. Any change in the patient load, such as the expected changes in body temperature and circulation, can be compensated for by the reactions of the automatic tuning systems.

Each applicator head can be operated at any desired power level which may or may not be the same as the power level of the other head. If the two applicator heads are operating at different power levels, different pulse widths are required on the key lines 30 of the two systems. Even so, there is no interference between the two applicator heads and no upsetting of the tuning or power sense systems because of the coherence in the phase and frequency of the RF energy applied to and radiated from the two heads.

The two applicator heads can be connected by cable 104 rather than cable 102. In this case, the master oscillator of System #2 is disabled and the oscillator of System #1 drives both systems. With cable 104 connecting the A2 terminal 20 of System #1 with the A1 terminal 18 of System #2, the dc line 56 of System #1 is coupled through resistor 58, choke 66, the A2 terminal of System #1, the cable 104, the A1 terminal of System #2 and choke 62 and control line 63 to the base of transistor 52 of System #2. This disable signal switches transistor 52 off and disables the master oscillator 12 of System #2.

The master oscillator 12 of System #1 is enabled (since its A1 terminal 18 is an open circuit), and its RF output energy is amplified and coupled to the #1 applicator head. Also, the RF energy on the buffer output line 48 of System #1 is coupled through capacitor 70, the A2 terminal of system #1, the cable 104, the A1 terminal of System #2 and through capacitors 68 and 50 to the base of the System #2 transistor 72. This signal is amplified and then coupled to the applicator head of System #2.

In this fashion, the applicator heads can be used simultaneously in close proximity with the oscillator of either system serving as the primary drive, depending upon how the terminals of the two systems are connected. If desired, the coaxial cables 102 and 104 can both be disconnected so that the two heads can be used separately, each with its own oscillator providing the RF drive energy.

The sizes of the coupling capacitors 50, 68 and 70 and the length of the coaxial cables 102 and 104 must be carefully selected if the diathermy equipment is to function effectively as a two head system. The values of the capacitances must be large enough to power match the output of the buffer transistor 46 so that both of the preamplifier transistors 72 can be driven by the RF output from one oscillator and buffer with full saturation of the power amplifiers maintained. Conversely, if the capacitances are too large, the preamplifier 72 can be overdriven when only one system is used. Perhaps even more importantly, the energy radiated from the applicator head can couple back excessively through the coaxial cables 102 and 104 to the base of transistor 72, causing regeneration of the system. Similarly, the coaxial cables should not be so long that they pick up an excessive amount of feedback, and they should not be so short that a mismatch is created making it impossible to effectively couple RF energy at 27 megahertz from the collector of transistor 46 to the base of transistor 72 of the other diathermy system. The particular range of power at which the diathermy treatment heads are designed to operate determines the capacitor values and cable lengths, along with other variables.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A method of using a pair of diathermy applicator heads each driven by an oscillator and a drive circuit coupling the oscillator to the corresponding applicator head to apply RF energy thereto, said method comprising the steps of:
    disabling one oscillator while enabling the other oscillator; and
    electrically coupling the drive circuits together to effect application of RF energy from said other oscillator to both drive circuits to drive each applicator head with RF energy which is coherent in phase and frequency, thereby permitting the applicator heads to be used simultaneously in close proximity to one another without substantial interaction caused by phase or frequency differences.

2. A method as set forth in claim 1, including the step of controlling each drive circuit independently in a manner to independently control the amount of power applied to each applicator head, whereby different amounts of power can be applied to each applicator head while maintaining phase and frequency coherence in the energy applied to the applicator heads.

3. Diathermy apparatus comprising:
    a pair of applicator heads each operable when energized to apply short wave RF energy to the body for therapeutic purposes;
    a drive circuit for each applicator head;
    oscillator means for each drive circuit for generating RF energy when enabled;
    means including an electrical conductor in each drive circuit for applying said RF energy to the corresponding applicator head to energize same for application of short wave energy to the body, whereby each applicator head can be used independently of the other applicator head; and
    means for selectively and releasably coupling the conductor of one drive circuit with the conductor of the other drive circuit and disabling the oscillator means of said other drive circuit while the conductors are coupled, whereby both applicator heads receive RF energy from the oscillator means of said one circuit to effect coherence in the energy applied to the applicator heads permitting them to be used in close proximity without substantial interaction.

4. Apparatus as set forth in claim 3, including:
    adjustable means for each drive circuit for cycling the circuit between an active condition wherein RF energy applied to the drive circuit is applied to the corresponding applicator head and an inactive condition wherein the corresponding applicator head is deenergized, each keying means being independent of the other keying means to permit each applicator head to operate at a different power level than the other applicator head.

5. In a diathermy apparatus having an applicator head for applying RF energy to a patient when energized, an improved drive circuit comprising:
    oscillator means for generating RF energy when enabled;
    buffer means coupled with said oscillator means to receive RF energy therefrom, said buffer means having a buffer output line carrying a buffered output signal when RF energy is applied to said buffer means;

amplifier means driven by said buffer output line in a manner to energize the applicator head when said buffered output signal is present on the buffer output line;

switch means for normally enabling said oscillator means, said switch means having a control line acting to disable said oscillator means in response to application of a disable signal to said control line;

a first terminal coupled with said buffer output line;

a second terminal coupled with said control line and with said buffer output line; and means for applying said disable signal to said first terminal and blocking application of the disable signal from the first terminal to the second terminal, whereby the first terminal of one drive circuit can be electrically connected to the second terminal of another drive circuit to establish a first circuit path applying said disable signal to the control line of said other drive circuit to disable the oscillator means thereof and a second path from the buffer output line of said one drive circuit to the buffer output line of said other drive circuit to apply the buffered output signal of said one drive circuit to the amplifier means of both drive circuits.

6. A drive circuit as set forth in claim 5, including:

adjustable keying means for cycling said amplifier means between an active condition wherein the applicator head is energized when said buffered output signal is present on the buffer output line and an inactive condition wherein the applicator head is deenergized, whereby the cycle of said keying means controls the output power of the applicator head.

7. A drive circuit as set forth in claim 5, wherein said switch means includes:

a power source connected with said oscillator means to normally enable same; and a switch element between said power source and oscillator means for controlling the connection therebetween, said switch element being normally conductive to provide a circuit path from the power source to said oscillator and being nonconductive to disconnect said power source from said oscillator means when said disable signal is applied to said control line.

8. A drive circuit as set forth in claim 5, including:

a conductor carrying said disable signal and connected with said first terminal to provide said disable signal applying means; and a blocking capacitor connected between said first and second terminals to block application of the disable signal from the first terminal to the second terminal.

9. In a diathermy apparatus having a pair of applicator heads each operable when energized to apply RF energy to a patient for therapeutic purposes, the improvement comprising:

a drive circuit for each applicator head having oscillator means for generating RF energy when enabled and buffer means driven by said RF energy, each buffer means having a buffer output line to which a buffered output signal is applied when the corresponding oscillator means generates RF energy;

amplifier means in each drive circuit for energizing the corresponding applicator head, each amplifier means having an active condition in which the corresponding applicator head is energized in response to the presence of a buffered output signal on the corresponding buffer output line and an inactive condition in which the corresponding applicator head is deenergized;

adjustable keying means for cycling each amplifier means between the active and inactive conditions to control the amount of power delivered to each applicator head, each keying means being independent of the other keying means; and means for coupling said drive circuits together in a manner to disable the oscillator means of one drive circuit and to electrically couple the buffer output lines of the drive circuits, whereby the amplifier means of both drive circuits are driven by the RF energy generated by the oscillator means of the other drive circuit to effect phase and frequency coherence in the energy applied to the applicator heads while permitting different amounts of power to be applied thereto.

* * * * *